(12) United States Patent
Hong et al.

(10) Patent No.: US 11,248,017 B2
(45) Date of Patent: Feb. 15, 2022

(54) ANTI-INFLAMMATORY COMPOSITION INCLUDING NOVEL KAEMPFEROL-BASED COMPOUND DERIVED FROM POST-FERMENTED TEA

(71) Applicant: AMOREPACIFIC CORPORATION, Seoul (KR)

(72) Inventors: Yong-Deog Hong, Yongin-si (KR); Jeong-Kee Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 67 days.

(21) Appl. No.: 16/622,100

(22) PCT Filed: Jun. 11, 2018

(86) PCT No.: PCT/KR2018/006608
§ 371 (c)(1),
(2) Date: Dec. 12, 2019

(87) PCT Pub. No.: WO2018/230909
PCT Pub. Date: Dec. 20, 2018

(65) Prior Publication Data
US 2020/0115409 A1 Apr. 16, 2020

(30) Foreign Application Priority Data
Jun. 12, 2017 (KR) .................. 10-2017-0073264

(51) Int. Cl.
*A61K 36/82* (2006.01)
*C07H 17/07* (2006.01)
*A61P 29/00* (2006.01)

(52) U.S. Cl.
CPC .............. *C07H 17/07* (2013.01); *A61P 29/00* (2018.01); *A61K 36/82* (2013.01); *A61K 2236/33* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 4,753,929 A | 6/1988 | Matsumoto et al. | |
| 2002/0165169 A1 | 11/2002 | Kim et al. | |
| 2012/0100087 A1 | 4/2012 | Chang et al. | |

FOREIGN PATENT DOCUMENTS

| | | |
|---|---|---|
| JP | 2008-208073 A | 9/2008 |
| KR | 10-0975199 B1 | 8/2010 |
| KR | 10-2012-0061733 A | 6/2012 |
| KR | 10-2013-0131095 A | 12/2013 |
| KR | 10-1418788 B1 | 7/2014 |
| KR | 10-2016-0103655 A | 9/2016 |
| WO | 90/06104 A1 | 6/1990 |
| WO | 2008/026507 A1 | 3/2008 |

OTHER PUBLICATIONS

Chatterjee et al. (2012) J. Adv. Pharma Tech and Res. vol. 3, Issue 2: 136-138. (Year: 2012).*
Chaudhuri et al. (2005) Pharmaceutical Research, 51: 169-175. (Year: 2005).*
Devi et al. (2015) Pharmacological Res. 99: 1-10 (Year: 215).*
Li et al. (2013) Food Funct. 4: 10-18. (Year: 2013).*
Enos Tangke Arung, et al., "Tyrosinase inhibitory effect of quercetin 4'-O-β-D-glucopyranoside from dried skin of red onion (*Allium cepa*)", Natural Product Research, 2011, vol. 25, No. 3, pp. 256-263.
Yang Zhao, et al., "Tentative identification, quantitation, and principal component analysis of green pu-erh, green, and white teas using UPLC/DAD/MS", Food Chemistry, 2011, vol. 126, No. 3, pp. 1269-1277.
Hai-peng Lv, et al., "Processing and chemical constituents of Pu-erh tea: A review", Food Research International, 2013, vol. 53, pp. 608-618.
Non-Final Office Action from U.S. Appl. No. 16/340,920, dated Jan. 22, 2020.
Atsuko Itoh, et al., "Flavonoid Glycosides from Adina racemosa and Their Inhibitory Activities on Eukaryotic Protein Synthesis", Journal of Natural Products, 2004, vol. 67, No. 3, pp. 427-431.
Hyun Gug Jung, et al., "Quercetin-3-O-β-D-glucopyranosyl-(1→6)-β-D-glucopyranoside suppresses melanin synthesis by augmenting p38 MAPK and CREB signaling pathways and subsequent cAMP down-regulation in murine melanoma cells", Saudi Journal of Biological Sciences, 2015, vol. 22, No. 6, pp. 706-713.
Md. Maniruzzaman Manir, et al., "Tea catechins and flavonoids from the leaves of Camellia sinensis inhibit yeast alcohol dehydrogenase", Bioorganic & Medicinal Chemistry, 2012, vol. 20, No. 7, pp. 2376-2381.
Yuping Tang, et al., "Coumaroyl flavonol glycosides from the leaves of Ginkgo biloba", Phytochemistry, 2001, vol. 58, pp. 1251-1256.
Xi-Feng Teng, et al., "Five New Flavonol Glycosides from the Fresh Flowers of Camellia reticulata", Helvetica Chimica Acta, Jul. 21, 2008, vol. 91, No. 7, pp. 1305-1312.
Lu-Rong Xu, et al., "A new acylated flavonol glycoside from Derris triofoliata" Journal of Asian Natural Products Research, 2006, vol. 8, No. 1-2, pp. 9-13.
G. W. Plumb, et al., "Antioxidant properties of flavonol glycosides from tea", Redox Report, 1999, vol. 4, No. 1-2, pp. 13-16.
Keith R. Price, et al., "Flavonol Glycoside Content and Composition of Tea Infusions Made from Commercially Available Teas and Tea Products", J. Agric. Food Chem., 1998, vol. 46, No. 7, pp. 2517-2522.
Yao Li, et al., "Quercetin, inflammation and immunity", Nutrients, 2016, vol. 8, No. 167, pp. 1-14.
Sheng-Kuo Hsieh, et al., "Identification of biosynthetic intermediates of teaghrelins and teaghrelin-like compounds in oolong teas, and their molecular docking to the ghrelin receptor", Journal of Food and Drug Analysis, 2015, vol. 23, pp. 660-670.

(Continued)

*Primary Examiner* — Russell G Fiebig
(74) *Attorney, Agent, or Firm* — Merchant & Gould P.C.

(57) ABSTRACT

The present specification relates to an anti-inflammatory composition including a novel compound isolated from a post-fermented tea, an isomer thereof, a pharmaceutically acceptable salt thereof, a hydrate thereof, or a solvate thereof, and may be widely used in various areas related to anti-inflammation.

15 Claims, 5 Drawing Sheets

(56) References Cited

OTHER PUBLICATIONS

Wu-Xia Bai, et al., "A Novel Acylated Flavonol Tetraglycoside with Inhibitory Effect on Lipid Accumulation in 3T3-L1 Cells from Lu'an GuaPian Tea and Quantification of Flavonoid Glycosides in Six Major Processing Types of Tea Running title: A Novel Acylated Flavonol Tetraglycoside Against Lipid Accumulation from Lu'an GuaPian Tea", Journal of Agricultural and Food Chemistry, 2017, vol. 65, No. 14, pp. 2999-3005.

Yuan-Hao Lo, et al., "Teaghrelins, Unique Acylated Flavonoid Tetraglycosides in Chin-Shin Oolong Tea, Are Putative Oral Agonists of the Ghrelin Receptor", J. Agric. Food Chem., 2014, vol. 62, pp. 5085-5091.

Zhenzhong Yang, et al., "An ultrafiltration high-performance liquid chromatography coupled with diode array detector and mass spectrometry approach for screening and characterising tyrosinase inhibitors from mulberry leaves", Analytica Chimica Acta, 2012, vol. 719, pp. 87-95.

International Search Report and Written Opinion from International Application No. PCT/KR2018/006602, dated Sep. 28, 2018.
International Search Report and Written Opinion from International Application No. PCT/KR2018/006605, dated Sep. 13, 2018.
International Search Report and Written Opinion from International Application No. PCT/KR2018/006608, dated Sep. 20, 2018.
International Search Report and Written Opinion from International Application No. PCT/KR2018/006609, dated Sep. 14, 2018.

* cited by examiner

ANTI-INFLAMMATORY COMPOSITION INCLUDING NOVEL KAEMPFEROL-BASED COMPOUND DERIVED FROM POST-FERMENTED TEA

CROSS-REFERENCE TO RELATED APPLICATION

This application is a National Stage Application of International Application No. PCT/KR2018/006608, filed Jun. 11, 2018, which claims benefit of Serial No. 10-2017-0073264, filed Jun. 12, 2017 in the Republic of Korea and which applications are incorporated herein by reference. To the extent appropriate, a claim of priority is made to each of the above disclosed applications.

TECHNICAL FIELD

The present specification relates to an anti-inflammatory composition including a novel kaempferol-based compound.

BACKGROUND ART

Inflammation is a series of defensive responses to an injury which has occurred to minimize the response if a cell or tissue is damaged by some causes and restore the damaged area to its original state, and causes nerve and blood vessels, lymphatic vessels, humoral responses, and cellular reactions, eventually resulting in pain, edema, redness, and fever, and thus causing dysfunction. The causes of inflammation include physical factors such as trauma, frostbite, burns, radiation, chemical factors such as acids, and immunological factors such as antibody reactions. In addition, inflammation is also caused by blood vessels or hormonal imbalances. Vasodilation is caused by various chemical mediators secreted by cells damaged by external stimuli, and as permeability increases, antibodies, complement, plasma, and phagocytic cells flock to the area of inflammation. This phenomenon causes erythema. Oxidative stress or the like, such as ultraviolet rays, active oxygen, free radicals or the like activates inflammatory factors and such inflammation causes various diseases and aging of the skin. One of the characteristics of inflammation is the increased oxygenation reaction of arachidonic acid, which is metabolized by the cyclooxygenase (COX) producing prostaglandins and the 5-lipoxygenase pathway producing leukotriene. Prostaglandins and leukotrienes are mediators of inflammation. Accordingly, cyclooxygenase enzymes include two forms of cyclooxygenase-1 and cyclooxygenase-2. The latter form, namely, cyclooxygenase-2, appears to play an important role in the progression of inflammation. Accordingly, inhibiting cyclooxygenase-2 enzyme may be an effective way to reduce inflammation without the side effects associated with irreversible cyclooxygenase-1 inhibition.

Green tea is drinkable in the form of leaf tea, or fermented tea for a deeper flavor. Fermented green tea means that the green tea leaves are subjected to oxidation treatment, and includes fermented tea oxidized by the oxidase present in the tea leaves, and post-fermented tea fermented by a separate microorganism other than the enzyme present in the tea leaves. Depending on the degree of fermentation, it can be classified into weakly fermented tea, semi-fermented tea, and fully fermented tea. For example, fermented green tea is called by various names, such as green tea, Oolong tea, black tea, puer tea, etc., depending on the type and extent of fermentation.

The fermented tea may not only show a difference in flavor compared to leaf tea, but may also show a big difference in the type and content of active ingredients depending on the specific fermentation process and the type of microorganism. Since various compounds can be produced and separated, various efforts for separating and identifying unknown novel compounds using green tea have been continued.

CITATION LIST

Patent Literature

[Patent Literature 1] Korean Patent No. 10-0975199

SUMMARY OF INVENTION

Technical Problem

In an aspect, an object of the present disclosure is to provide a novel compound derived from post-fermented tea for anti-inflammatory use.

Solution to Problem

In one embodiment, the present disclosure provides an anti-inflammatory composition including a compound of Formula 1, an optical isomer thereof, a pharmaceutically acceptable salt thereof, a hydrate thereof, a solvate thereof, or a post-fermented tea extract comprising the same as an active ingredient.

[Formula 1]

In Formula 1 above, $R_1$ may be $C_{15}H_9O_6$, $R_2$ may be $C_6H_{11}O_5$, and $R_3$ may be $C_9H_7O_2$.

In another aspect of the present disclosure, the composition may be a composition that inhibits the production of one or more selected from the group consisting of $PGE_2$ (Prostaglandin $E_2$), IL-6 (Interleukin 6) and IL-8 (Interleukin 8)

In one embodiment, the present disclosure provides a method for anti-inflammation comprising administering a compound of Formula 1, an optical isomer thereof, a pharmaceutically acceptable salt thereof, a hydrate thereof, a solvate thereof, or a post-fermented tea extract comprising the same to a subject in need thereof.

In one embodiment, the present disclosure provides a use of a compound of Formula 1, an optical isomer thereof, a pharmaceutically acceptable salt thereof, a hydrate thereof, a solvate thereof, or a post-fermented tea extract comprising the same in manufacture of a composition for anti-inflammation.

In one embodiment, the present disclosure provides a compound of Formula 1, an optical isomer thereof, a pharmaceutically acceptable salt thereof, a hydrate thereof, a solvate thereof, or a post-fermented tea extract comprising the same for use in anti-inflammation.

Advantageous Effects of Invention

In one aspect, the present disclosure can be widely used in post-fermented tea-related industries, anti-inflammatory related fields, or the like, by allowing novel compounds isolated from post-fermented tea to be used in anti-inflammatory fields.

DESCRIPTION OF EMBODIMENTS

Hereinafter, the present disclosure will be described in detail.

As used herein, "post-fermentation" includes fermentation by a separate microorganism or substance other than the enzyme present in tea leaves. Post-fermented tea includes green tea fermented by the above method.

As used herein, the term "extract" means a substance obtained by extracting a component contained inside of a natural substance, regardless of the extracted method or ingredients.

The term is used in a broad sense including, for example, extracting a component soluble in a solvent from a natural substance using water or an organic solvent, extracting only a specific component of a natural substance such as oil, and fraction that fractionated those thus obtained again by using a specific solvent or the like.

As used herein, fractions include those obtained by fractionating a specific substance or extract using a certain solvent or those left after fractionating, and extracting them again with a specific solvent. Fractional methods and extraction methods may be any method known to those skilled in the art.

As used herein, "isomers" include, in particular, not only optical isomers (e.g., essentially pure enantiomers, essentially pure diastereomers or mixtures thereof), but also conformation isomers (i.e., isomers that differ only in their angles of one or more chemical bonds), position isomers (especially tautomers) or geometric isomers (e.g., cis-trans isomers).

As used herein, the term "essentially pure" means that a specific compound, for example enantiomers or diastereomers, when used in connection with an enantiomer or diastereomer, is present in an amount of at least about 90%, preferably at least about 95%, more preferably at least about 97% or at least about 98%, even more preferably at least about 99%, and even more further preferably at least about 99.5% (w/w).

As used herein, the term "pharmaceutically acceptable" refers to those that can be approved or approved by the government or equivalent regulatory agencies for use in animals, more specifically in humans, by avoiding significant toxic effects when used in conventional medicinal dosage, or those recognized as being listed in the pharmacopoeia or described in other general pharmacopoeia.

As used herein, the term "pharmaceutically acceptable salt" refers to a salt according to one aspect of the present disclosure that is pharmaceutically acceptable and possesses the desired pharmacological activity of the parent compound. The salts include (1) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, or the like; or (2) salts formed when an acidic proton present in the parent compound is substituted.

As used herein, the term "hydrate" refers to a compound to which water is bound, and is a broad concept including an inclusion compound having no chemical bonding force between water and the compound.

As used herein, the term "solvate" refers to a compound of higher order produced between molecules or ions of a solute and molecules or ions of a solvent.

In one aspect, the present disclosure provides an anti-inflammatory composition including a compound of following Formula 1, an optical isomer thereof, a pharmaceutically acceptable salt thereof, a hydrate thereof, a solvate thereof, or a post-fermented tea extract comprising the same as an active ingredient.

[Formula 1]

In Formula 1 above, $R_1$ may be $C_{15}H_9O_6$, $R_2$ may be $C_6H_{11}O_5$, and $R_3$ may be $C_9H_7O_2$.

In one embodiment, $R_1$ may be a compound of following Formula 2.

[Formula 2]

In another embodiment, R₂ may be a compound of following Formula 3.

[Formula 3]

R₃ may be a compound of following Formula 4.

[Formula 4]

In another embodiment, the compound may be kaempferol3-O-[2-O"-(E)-p-coumaroyl][beta-D-glucopyranosyl-(1→3)-O-alpha-L-rhamnopyranosyl-(1→6)-O-beta-D-glucopyranoside]). The compound may be represented by following Formula 5.

[Formula 5]

According to one aspect of the present disclosure, a method for preparing the compounds, isomers thereof, pharmaceutically acceptable salts thereof, hydrates thereof or solvates thereof may include synthesis, separation from natural substances, or the like.

According to another embodiment, the post fermentation may be by strain inoculation, and the strain may be selected from *Saccharomyces* sp., *Bacillus* sp., *Lactobacillus* sp., and *Leuconostoc mesenteroides* sp., and may preferably be selected from *Saccharomyces cerevisiae, Lactobacillus casei, Bacillus subtlis, Lactobacillus bulgarius* and *Leuconostoc mesenteroides*. According to another embodiment, the post-fermented tea may be post-fermented green tea.

In one aspect of the present disclosure, the compound is a compound discovered by the present inventors after the continuous studies of the post-fermented tea, and it was confirmed that the compound is effective in inhibiting the production of one or more selected from the group consisting of $PGE_2$ (Prostaglandin $E_2$), IL-6 (Interleukin 6) and IL-8 (Interleukin 8). Accordingly, it has been demonstrated that the compounds can be used for the purpose of inhibiting, preventing, treating or ameliorating inflammation using the compounds according to one aspect of the present disclosure.

In one embodiment, the extraction may be extraction by one or more solvents selected from water, hydrothermal water, lower alcohols of $C_1$ to $C_6$, and mixed solvents thereof, and in another embodiment, the lower alcohol may be an alcohol alone or a mixture which can be generally used in the art, and may preferably be ethanol.

According to another aspect of the present disclosure, the extract may be a fraction fractionated with ketones after extraction.

In another embodiment, examples of the ketones include acetone, carvon, pulegone, isolongifolanone, 2-heptanone, 2-pentanone, 3-hexanone, 3-heptanone, 4-heptanone, 2-octanone, 3-octanone, 2-nonanone, 3-nonanone, 2-undecanone, 2-tridecanone, methyl isopropyl ketone, ethyl isoamyl ketone, butylidene acetone, methylheptenone, dimethyl octenone, geranyl acetone, farnesyl acetone, 2,3-pentadione, 2,3-hexadione, 3,4-hexadione, 2,3-heptadione, amylcyclopentanone, amylcyclopentenone, 2-cyclopentyl cyclopentanone, hexylcyclopentanone, 2-n-heptylcyclopentanone, cis-jasmon, dihydrojasmon, methylcorylone, 2-tert-butylcyclohexanone, p-tert-butylcyclohexanone, 2-sec-butylcyclohexanone, celery ketone, krypton, p-tert-pentylcyclohexanone, methylcyclocitron, neron, 4-cyclohexyl-4-methyl-2-pentanone, oxide ketone, emoxyprone, methylnaphthyl ketone, α-methylanisal acetone, anisyl acetone, p-methoxy phenyl acetone, benzylidene acetone, p-methoxyacetophenone, p-methylacetophenone, propiophenone, acetophenone, α-dynascone, lritone, ionone, pseudoionone, methylionone, methyl lritone, 2,4-di-tert-butylcyclohexanone, allylionone, 2-acetyl-3,3-dimethylnorbornane, verbenone, fenchon, cyclopentadecanone, cyclohexadecenone, or the like, may include both ketones and mixtures thereof as solvents that can be generally used in the art, and may preferably be acetone.

According to one aspect of the present disclosure, the content of the compound of Formula 1, an isomer thereof, a pharmaceutically acceptable salt thereof, a hydrate thereof, or a solvate thereof in the composition may be 0.00001% to 10% by weight based on the total weight of the composition. The content may be at least 0.00001% by weight, at least 0.00005% by weight, at least 0.0001% by weight, at least 0.0005% by weight, at least 0.001% by weight, at least 0.005% by weight, at least 0.01% by weight, at least 0.05% by weight, at least 0.1% by weight, at least 0.5% by weight, at least 1% by weight, at least 2% by weight, at least 3% by weight, at least 4% by weight, at least 5% by weight, at least 6% by weight, at least 7% by weight, at least 8% by weight, or at least 9% by weight. In addition, the content may be 10% or less by weight, 9% or less by weight, 8% or less by weight, 7% or less by weight, 6% or less by weight, 5% or less by weight, 4% or less by weight, 3% or less by weight, 2% or less by weight, 1% or less by weight, 0.5% or less by weight, 0.1% or less by weight, 0.05% or less by weight, 0.01% or less by weight, 0.005% or less by weight, 0.001% or less by weight, 0.0005% or less by weight, 0.0001% or less by weight, 0.00005% or less by weight, or 0.00003% or less by weight.

According to another aspect of the present disclosure, the content of the post-fermented tea extract in the composition may be 0.1% to 90% by weight based on the total weight of the composition. The content may be at least 0.1% by weight, at least 1% by weight, at least 5% by weight, at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, or at least 85% by weight based on the total weight of the composition. In addition, the content may be 90% or less by weight, 85% or less by weight, 80% or less by weight, 75% or less by weight, 70% or less by weight, 65% or less by weight, 60% or less by weight, 55% or less by weight, 50% or less by weight, 45% or less by weight, 40% or less by weight, 35% or less by weight, 30% or less by weight, 25% or less by weight, 20% or less by weight, 15% or less by weight, 10% or less by weight, 5% or less by weight, 1% or less by weight, or 0.5% or less by weight.

According to another aspect of the present disclosure, the extract may contain the compound of Formula 1, an isomer thereof, a pharmaceutically acceptable salt thereof, a hydrate thereof, or a solvate thereof in an amount of at least 0.00001% by weight, at least 0.00005% by weight, at least 0.0001% by weight, at least 0.0005% by weight, at least 0.001% by weight, at least 0.005% by weight, at least 0.01% by weight, at least 0.05% by weight, at least 0.1% by weight, at least 0.5% by weight, at least 1% by weight, at least 3% by weight, at least 5% by weight, at least 7% by weight, at least 10% by weight, at least 12% by weight, at least 15% by weight, or at least 18% by weight based on the total weight of the extract. In addition, the content may be 20% or less by weight, 15% or less by weight, 12% or less by weight, 10% or less by weight, 7% or less by weight, 5% or less by weight, 3% or less by weight, 1% or less by weight, 0.5% or less by weight, 0.1% or less by weight, 0.05% or less by weight, 0.01% or less by weight, 0.005% or less by weight, 0.001% or less by weight, 0.0005% or less by weight, 0.0003% or less by weight, 0.00005% or less by weight, or 0.00003% or less by weight. Preferably, the extract may contain 0.00001% to 20% by weight of the compound of Formula 1, an isomer thereof, a pharmaceutically acceptable salt thereof, a hydrate thereof, or a solvate thereof based on the total weight of the extract.

According to another aspect of the present disclosure, the dosage of the compound of Formula 1, an isomer thereof, a pharmaceutically acceptable salt thereof, a hydrate thereof, or a solvate thereof by administration of the composition may be 0.00001 mg/kg/day to 100 mg/kg/day. The dosage may be at least 0.00001 mg/kg/day, at least 0.0001 mg/kg/day, at least 0.001 mg/kg/day, at least 0.005 mg/kg/day, at least 0.01 mg/kg/day, 0.05 mg/kg/day, at least 0.1 mg/kg/day, at least 0.5 mg/kg/day, at least 1 mg/kg/day, at least 5 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, at least 50 mg/kg/day, at least 55 mg/kg/day, at least 60 mg/kg/day, at least 65 mg/kg/day, at least 7 mg/kg/day, at least 75 mg/kg/day, at least 80 mg/kg/day, at least 85 mg/kg/day, at least 90 mg/kg/day, or at least 95 mg/kg/day. In addition, the dosage may be 100 mg/kg/day or less, 95 mg/kg/day or less, 90 mg/kg/day or less, 85 mg/kg/day or less, 80 mg/kg/day or less, 75 mg/kg/day or less, 70 mg/kg/day or less, 65 mg/kg/day or less, 60 mg/kg/day or less, 55 mg/kg/day or less, 50 mg/kg/day or less, 45 mg/kg/day or less, 40 mg/kg/day or less, 35 mg/kg/day or less, 30 mg/kg/day or less, 25 mg/kg/day or less, 20 mg/kg/day or less, 15 mg/kg/day or less, 10 mg/kg/day or less, 5 mg/kg/day or less, 1 mg/kg/day or less, 0.5 mg/kg/day or less, 0.1 mg/kg/day or less, 0.05 mg/kg/day or less, 0.01 mg/kg/day or less, 0.005 mg/kg/day or less, 0.003 mg/kg/day or less, 0.001 mg/kg/day or less, 0.0005 mg/kg/day or less, 0.0001 mg/kg/day or less, 0.00005 mg/kg/day or less.

According to one embodiment, the inflammation may be due to production or increase of one or more selected from the group consisting of $PGE_2$ (Prostaglandin $E_2$), IL-6 (Interleukin 6) and IL-8 (Interleukin 8).

According to another aspect of the invention, the composition may be a food composition, a cosmetic composition, or a pharmaceutical composition.

Food composition according to one aspect of the present disclosure may be a health food composition. In the health food composition, the dosage determination of the compound is within the level of those skilled in the art, and may vary depending on a variety of factors including the age, health condition and complications, or the like of the subject to be administered.

The health food composition according to one aspect of the present disclosure may be a health functional food, as well as, for example, may be any form of processed food including various foodstuffs such as chewing gum, caramel product, candy, ice cream, confectionery, breads, or the like, beverages such as soft drinks, mineral water, alcoholic beverages, or the like, and may be functional foodstuffs including vitamins, minerals, or the like.

In addition to the above, the health food composition according to one aspect of the present disclosure may contain various nutrients, vitamins, minerals (electrolytes), flavors such as synthetic flavorings and natural flavorings, colorants and enhancers (cheese, chocolate, or the like), pectic acid and salts thereof, alginic acid and salts thereof, organic acids, protective colloid thickeners, pH adjusting agents, stabilizers, preservatives, glycerin, alcohols, and carbonating agents used in carbonated beverages. In addition, the functional food compositions of the present disclosure may contain natural fruit juice and flesh for the production of fruit juice drinks and vegetable drinks. These components may be used independently or in combination. The proportion of such additives is not so critical, but the additives are generally contained in the range of from 0 to about 50 parts by weight per 100 parts by weight of the composition according to one aspect of the present disclosure.

The cosmetic composition according to one aspect of the present disclosure is a composition for skin, nails and/or hair, and may have a formulation, for example, softening tonic, astringent tonic, nourishing tonic, nourishing cream, massage cream, eye cream, eye essence, essence, cleansing cream, cleansing lotion, cleansing foam, cleansing water, pack, powder, body lotion, body cream, body essence, body cleanser, hair dye, shampoo, rinse, hair conditioner, hair tonic, ointment, gel, cream, patch, spray and skin adhesive type, or the like, but is not limited thereto.

In addition, in each formulation, other ingredients in addition to the above essential ingredients may be appropriately selected and blended by those skilled in the art without difficulties according to the kind or purpose of use of other external preparations.

The cosmetic composition may be provided in any formulation suitable for topical application. For example, it may be provided in forms of a solution, an emulsion obtained by dispersing an oil phase in an aqueous phase, an emulsion obtained by dispersing an aqueous phase in an oil phase, a suspension, a solid, a gel, a powder, a paste, a microneedle, a foam, or an aerosol composition. Compositions of such formulations may be prepared according to the conventional methods in the pertinent field.

The cosmetic composition according to the present specification may further include functional additives and components included in general cosmetic compositions in addition to the compounds, extracts or fractions of the present specification. The functional additive may include the components selected from the group consisting of water-soluble vitamins, oil-soluble vitamins, polymer peptides, polymer polysaccharides, sphingolipids and seaweed extracts. The cosmetic composition according to the present specification may include other components that can give a synergistic effect to the main effect, preferably within a range that does not impair the main effect. In addition, the cosmetic composition according to the present specification may further include a moisturizer, an emollient, a surfactant, a ultraviolet absorbent, a preservative, a bactericide, an antioxidant, a pH adjusting agent, an organic and an inorganic pigment, a perfume, a cooling agent, or a control agent. The blending amount of the components may be easily selected by those skilled in the art within the range that does not impair the purpose and effect of the present specification, and the blending amount may be 0.001% to 10% by weight, specifically 0.01% to 3% by weight based on the total weight of the composition. have.

According to another embodiment, the composition may be a composition for external skin application. The composition for external skin application may be a composition such as cosmetics, mouthwashes, cleaning agents, pharmaceuticals and quasi-drugs, but is not limited thereto. The external preparation for skin is not particularly limited in its formulation.

In addition, the composition for external skin application of the present specification may further include at least one selected from functional salts for a particular purpose and a pH adjusting agent for adjusting pH. In this case, the salt may be selected from inorganic salts, organic salts and/or organic-inorganic salts for ion shielding, moisturizing, UV protection, or the like. For a concrete example, the salt may be selected from sodium chloride (NaCl), sodium phosphate (Na3PO4), calcium chloride (CaCl2), or the like. The pH adjusting agent may be selected from the group consisting of acids and bases, for example hydrochloric acid, sulfuric acid, tartaric acid, citric acid, phosphoric acid, acetic acid, lactic acid, sodium lactate, sodium hydroxide, potassium hydroxide, alkyl amines, alkanol amine and ammonia.

The composition for external skin application of the present specification may be a cosmetic, pharmaceutical or quasi-drug composition, wherein the cosmetic, pharmaceutical or quasi-drug composition may additionally contain a preservative, stabilizer, hydrating agents or emulsificant, adjuvant such as salt and/or buffer for controlling osmotic pressure and other therapeutically useful substances. The composition may be formulated into a lotion, cream, ointment, gel, or the like. The composition for external skin application may preferably be administered transdermally.

The dosage of the active ingredient of the pharmaceutical or quasi-drug composition may vary depending on the age, sex, and weight of the subject to be treated, the specific disease or pathology to be treated, the severity of the disease or pathologic state, the route of administration, and the judgment of the prescriber. The determination of dosage based on these factors is within the level of those skilled in the art. In general, the dosage of the active ingredient may range from 0.00001 mg/kg/day to 15 mg/kg/day, but is not limited thereto.

The pharmaceutical composition according to one aspect of the present invention may be administered orally, parenterally, rectally, topically, transdermally, intravenously, intramuscularly, intraperitoneally, subcutaneously, or the like. Formulations for oral administration may be, but are not limited thereto, tablets, pills, soft and hard capsules, granules, powders, granules, solutions, emulsions or pellets. Formulations for parenteral administration may be, but are not limited to, solutions, suspensions, liquids, emulsions, gels, injections, drops, suppositories, patches or sprays. The formulations can be readily prepared according to conventional methods in the pertinent field, and may additionally contain surfactants, excipients, hydrating agents, emulsificants, suspending agents, salts or buffers for controlling osmotic pressure, colorants, spices, stabilizers, preservatives, preserved agents or other commercially available adjuvants.

The dose or dosage of the pharmaceutical composition according to one aspect of the present invention may vary depending on the age, sex, weight, pathologic state and severity of the subject to be administered, the route of administration or the judgment of the prescriber. The determination of the dose based on these factors is within the level of those skilled in the art.

The formulation of the food composition is not particularly limited, but may be, for example, formulated into tablets, granules, pills, powders, liquids such as drinks, caramels, gels, bars, tea bags, or the like. In addition to the active ingredient, the food composition of each formulation may appropriately select and mix the ingredients that are commonly used in the pertinent field according to the formulation or purpose of use by those skilled in the art without difficulty. Synergistic effects may occur when applied simultaneously with other raw materials.

The composition may be administered by various methods such as simple ingestion, drinking, injection administration, spray administration or squeeze administration, or the like.

Hereinafter, the configuration and effects of the present specification will be described in more detail with reference to the examples, experimental examples, and formulation examples.

However, these examples are provided only for the purpose of illustration in order to facilitate understanding of the present specification, and the scope and range of the present specification is not limited by the following examples.

EXAMPLES

[Example 1] Preparation of Post Fermented Tea Samples

The water content was adjusted to 40% by weight by adding water to the green tea made from green tea (*Camellia sinensis* var. Yabukita) leaves. Then $5 \times 10^6$ cfu/g of *Bacillus* subtillis was seeded, fermented at 50° C. for 3 days, and then fermented at 80° C. for 4 days.

The fermented tea sample was pulverized for 15 seconds and filtered through a stainless steel sieve of mesh size 1 mm. Then, 50 mg of the pulverized sample was added to 1.5 ml Eppendorf tube and 1 ml of deionized water was added and stirred at a constant speed for 30 minutes in a 60° C. constant temperature water bath, followed by centrifugation at 25° C., 13,000 rpm for 15 minutes. Only the portions insoluble in water in the centrifuged fermented green tea extract were separated.

[Example 2] Obtainment of Fractions and Separation of Compounds 150 g of the post-fermented tea sample was fractionated with acetone to remove catechin derivatives and caffeine and to obtain a soluble in which other compounds were concentrated. For 40 g of the acetone solubles, fractions were obtained primarily using a 5:1 (v/v) mixture of chloroform:methanol as a solvent using silica gel column chromatography.

8.9 g of the caffeine-free chloroform:methanol 5:1 (v/v) fraction was fractionated using large capacity high performance countercurrent chromatography (HPCCC, Dynamic Extractions Ltd, UK). The solvent used then was n-hexane-TBME(Methyl tert-butyl ether)-BuOH-MeCN-Water (0.25: 3:1:1:5, v/v), and the flow rate was 25 ml/min. A total of 10 subfractions were divided using the above conditions, and the components contained in each fraction was again separated using small capacity HPCCC (Dynamic Extractions Ltd, UK), High-performance liquid chromatography (HPLC), Sephadex LH-20 columns (GE Healthcare Bio-Sciences, Sweden), or the like.

As a result, kaempferol3-O-[2-O"-(E)-p-coumaroyl][beta-D-glucopyranosyl-(1→3)-O-alpha-L-rhamnopyranosyl-(1→6)-O-beta-D-glucopyranoside], a compound which was not known before, could be separated from the fractions. The structure of each compound was investigated by identifying the structure using $^1$H, $^{13}$C-NMR (nuclear magnetic resonance spectroscopy), UV (ultraviolet spectroscopy), and ESI-MS (Electro Spray Ionization Mass Spectroscopy). In the case of $^1$H and $^{13}$C nuclear magnetic resonance (NMR), methanol-d3 was used as a solvent, and Bruker Advance DPX-500 (BRUKER, USA) was used as a device. MS spectra of each compound were analyzed using 6200 Series Accurate-Mass Time-of-Flight (TOF) LC/MS (Agilent, US).

As a result of the analysis, each of the compound is a novel compound which was not known before, and was confirmed as kaempferol3-O-[2-O"-(E)-p-coumaroyl][beta-D-glucopyranosyl-(1→3)-O-alpha-L-rhamnopyranosyl-(1→6)-O-beta-D-glucopyranoside]('new material 33') having a molecular weight of 902.2481 of $C_{42}H_{46}O_{22}$.

The formula and NMR data of kaempferol3-O-[2-O"-(E)-p-coumaroyl][beta-D-glucopyranosyl-(1→3)-O-alpha-L-rhamnopyranosyl-(1→6)-O-beta-D-glucopyranoside] are as follows.

TABLE 1

| Position | $^{13}$C-NMR | $^1$H-NMR |
|---|---|---|
| 2 | 161.26 | |
| 3 | 135.07 | |
| 4 | 179.31 | |
| 5 | 161.5 | |
| 6 | 99.87 | 6.17 (H6, brs) |
| 7 | 165.74 | |
| 8 | 94.8 | 6.35 (H8, brs) |
| 9 | 158.58 | |
| 10 | 105.84 | |
| 1' | 122.72 | |
| 2', 6' | 132.29 | 7.99 (H2'/H6', d, J = 8.3 Hz) |
| 3', 5' | 116.27 | 6.87 (H3'/H5', d, J = 8.3 Hz) |
| 4' | 158.69 | |
| p-coumaric acid | | |
| 1''' | 127.3 | |
| 2''', 6''' | 131.2 | 7.45 (H2'''/H6''', d, J = 8.1 Hz) |
| 3''', 5''' | 116.82 | 6.80 (H3'''/H5''', d, J = 8.1 Hz) |
| 4''' | 161.26 | |
| 7''' | 115.31 | 6.35 (H7''', d, J = 15.7 Hz) |
| 8''' | 146.88 | 7.67 (H8''', d, J = 15.7 Hz) |
| C=O | 168.79 | |
| Glc1 | | |
| 1'' | 101.55 | 5.46 (H1'', d, J = 7.8 Hz) |
| 2'' | 74.14 | 5.34 (H2'', t, J = 9 Hz) |
| 3'' | 73.25 | 3.76 (H3'', d, J = 10.4 Hz) |
| 4'' | 70.47 | 3.85 (H4'', m) |
| 5'' | 75.51 | 3.73 (H5'', m) |
| 6'' | 67.54 | 3.76 (H6'', brd, J = 10.4 Hz) |
| | | 3.54 (H6'', m) |
| Rha | | |
| 1'''' | 101.85 | 4.60 (H1'''', brs) |
| 2'''' | 71.34 | 3.95 (2'''', m) |
| 3'''' | 83.09 | 3.61 (H3'''', dd, J = 9, 3 Hz) |
| 4'''' | 72.6 | 3.46 (H4'''', m) |
| 5'''' | 69.49 | 3.54 (H5'''', m) |
| 6'''' | 18.08 | 1.19 (H6'''', d, J = 6 Hz) |
| Glc2 | | |
| 1''''' | 105.74 | 4.40 (H1''''', d, J = 7.5 Hz) |
| 2''''' | 75.4 | 3.25 (H2''''', m) |
| 3''''' | 77.6 | 3.36 (H3''''', m) |
| 4''''' | 70.84 | 3.36 (H4''''', m) |
| 5''''' | 77.6 | 3.25 (H5''''', m) |
| 6''''' | 62.05 | 3.71 (H6''''', m) |

Figure 1:
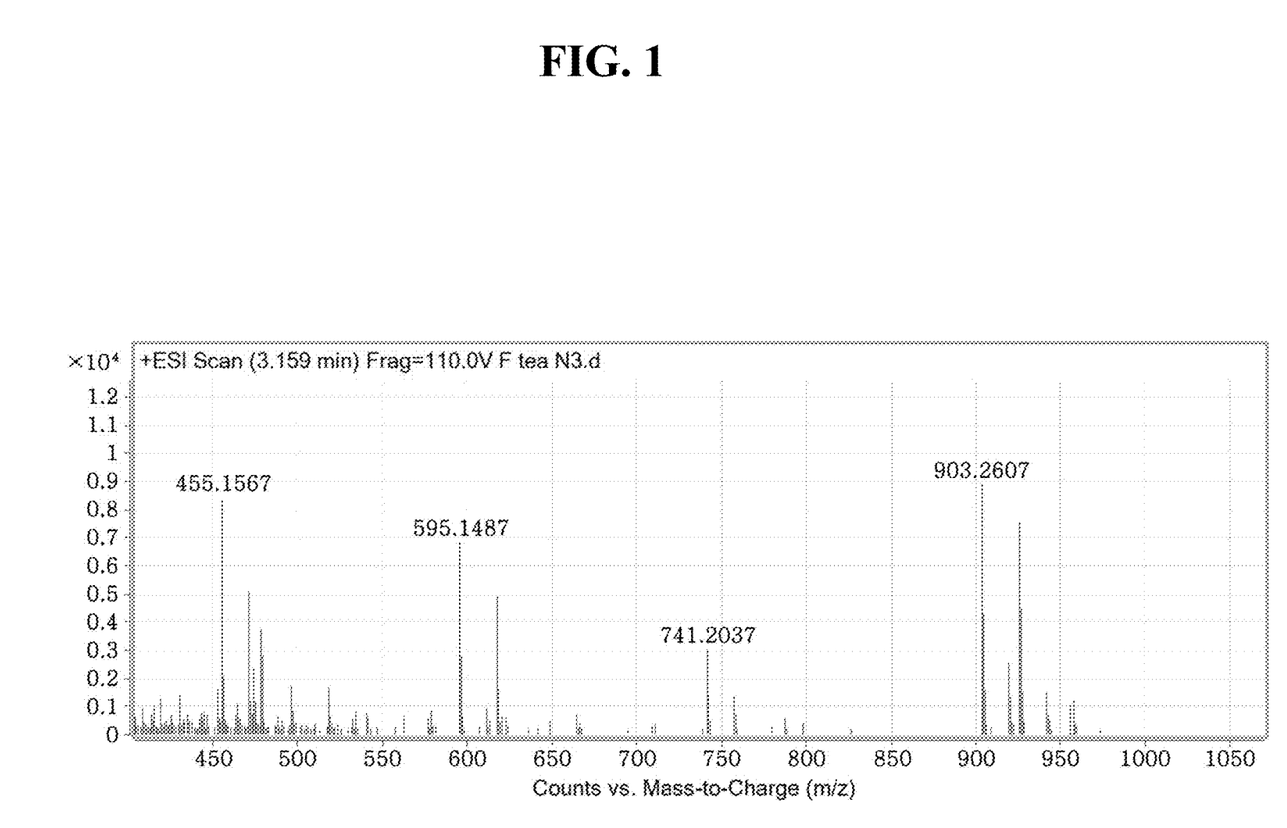
FIG. 1 shows an MS spectrum of the compound according to an aspect of the invention.
Figure 2:
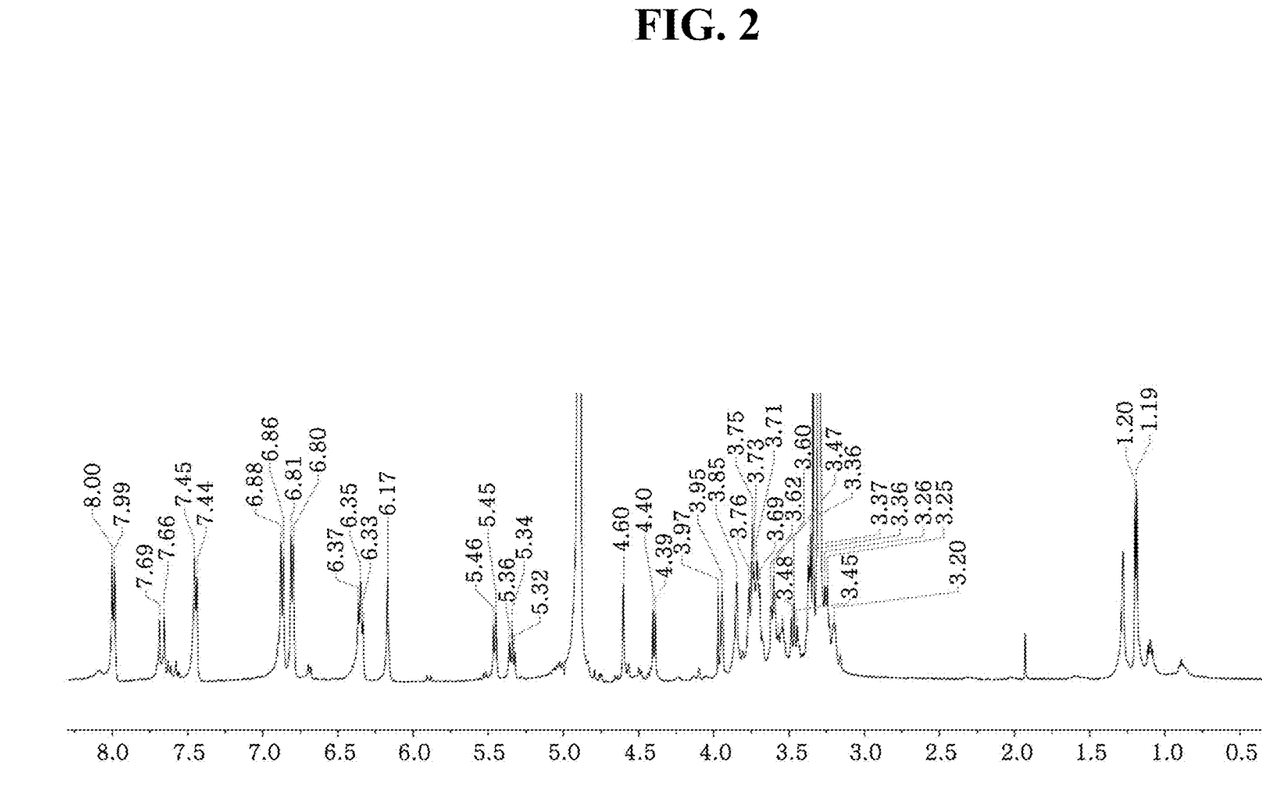
FIG. 2 shows a $^1$H-NMR (nuclear magnetic resonance) spectrum of the compound according to an aspect of the present disclosure.
Figure 3:
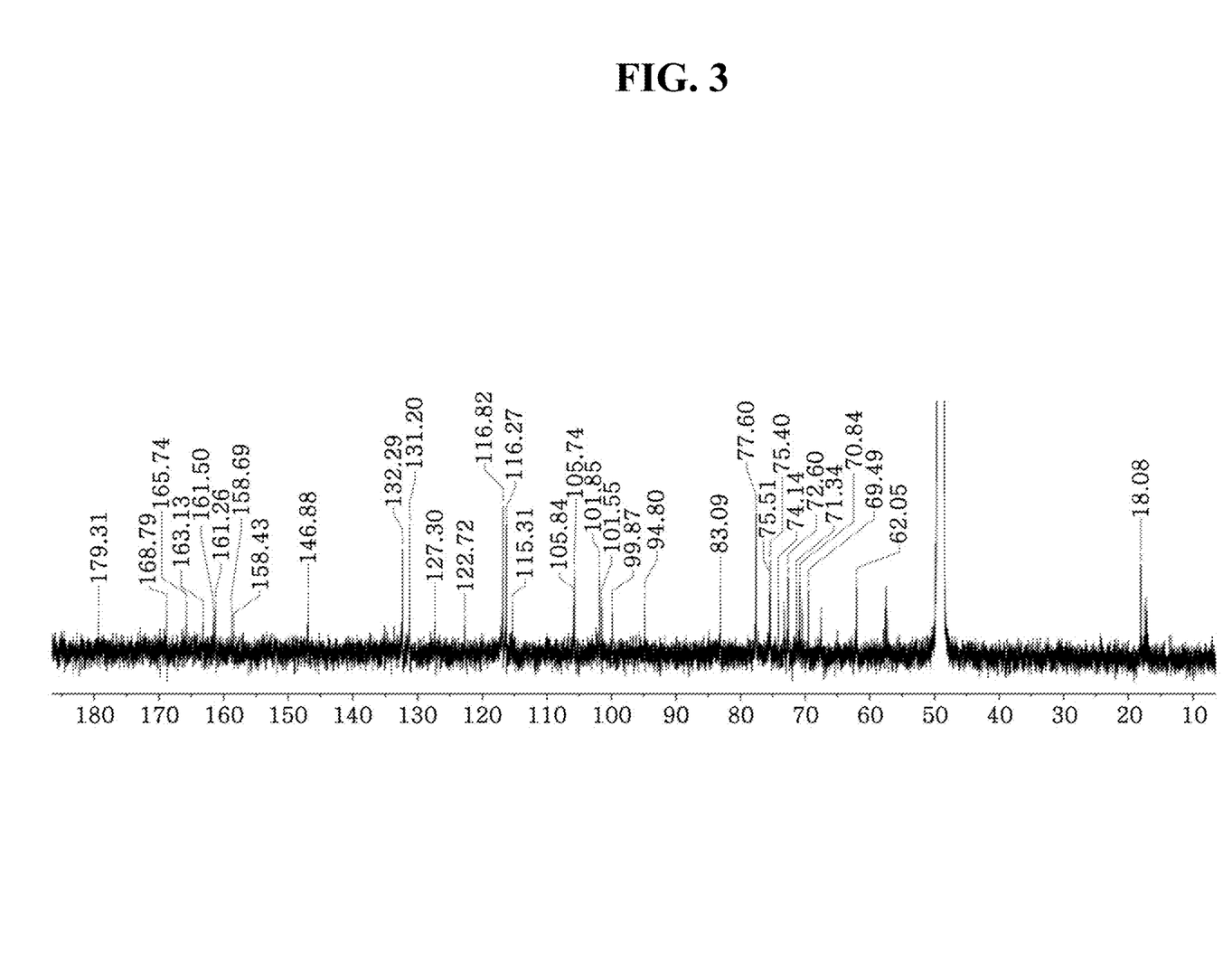
FIG. 3 shows a $^{13}$C-NMR spectrum of the compound according to an aspect of the present disclosure.
Figure 4:
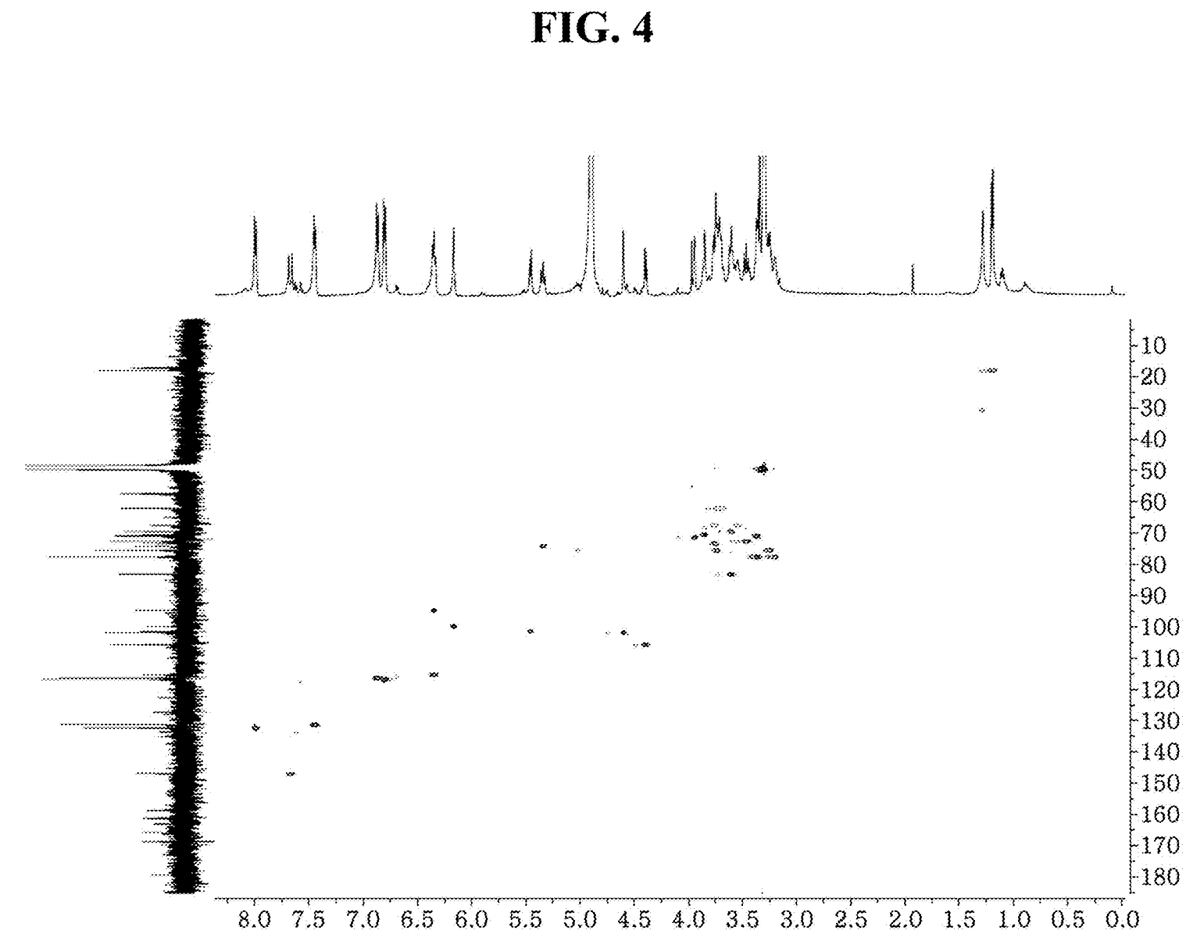
FIG. 4 shows an $^1$H-$^{13}$C HSQC (Heteronuclear Single Quantum Coherence) spectrum of the compound according to an aspect of the present disclosure.
Figure 5:
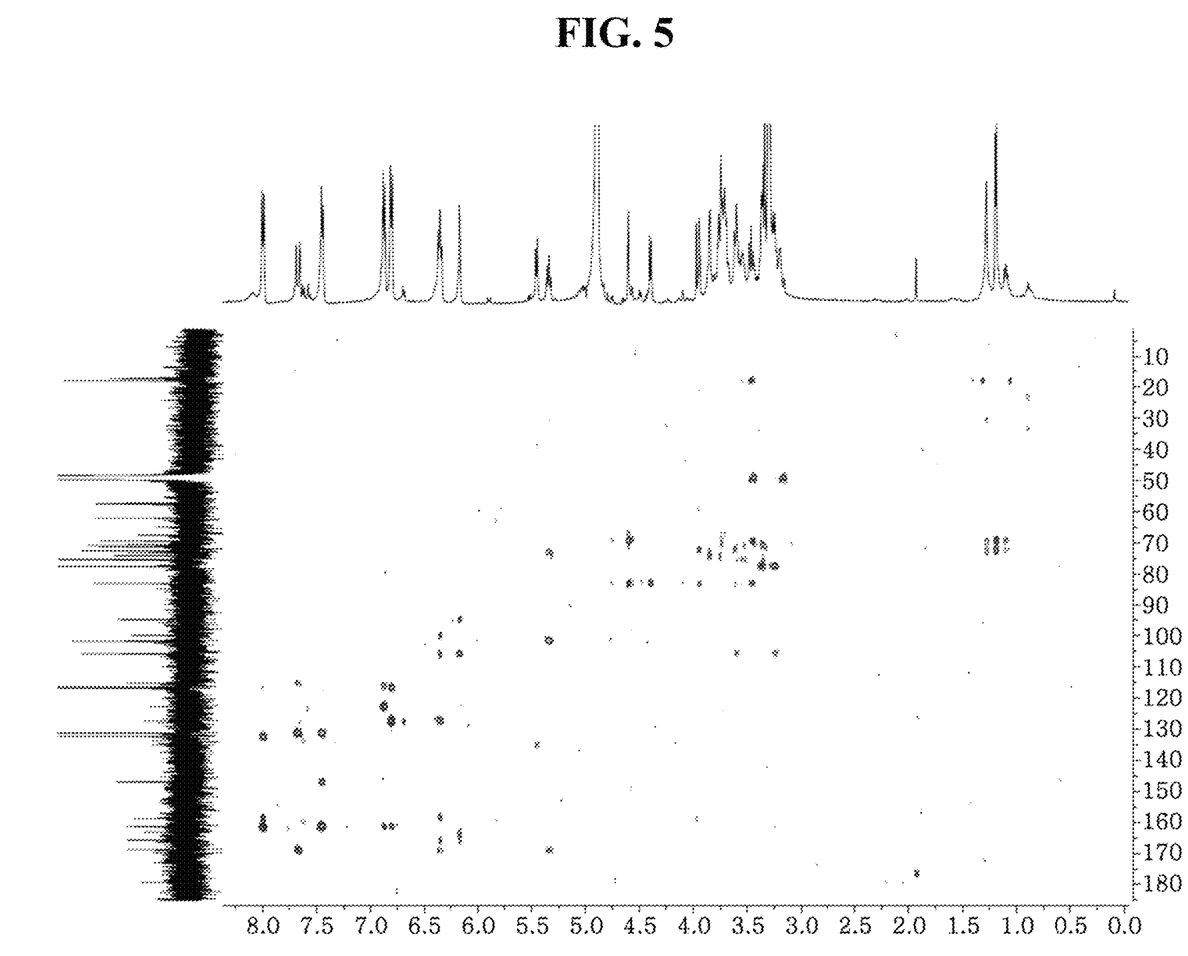
FIG. 5 shows a $^1$H-$^{13}$C HMBC (Heteronuclear Multiple-Bond Coherence) spectrum of the compound according to an aspect of the present disclosure.

The MS spectrum of kaempferol3-O-[2-O"-(E)-p-coumaroyl][beta-D-glucopyranosyl-(1→3)-O-alpha-L-rhamnopyranosyl-(1→6)-O-beta-D-glucopyranoside] is as shown in FIG. 1, $^1$H-NMR spectrum and $^{13}$C-NMR spectrum are as shown in FIGS. 2 and 3, respectively, HSQC (Heteronuclear Single Quantum Coherence) spectrum is as shown in FIG. 4, and HMBC (Heteronuclear Multiple-Bond Coherence) spectrum is as shown in FIG. 5.

[Experimental Example 1] PGE2, IL-6 and IL-8 Production Inhibition Experiment

Human fibroblasts (PromoCell, Germany) were seeded into 6-well culture plates at a concentration of $1\times10^5$ cells and incubated in 37° C., 5% $CO_2$ incubator for 24 hours. After 500 μM of $H_2O_2$ was treated in a well and stimulated for 24 hours, the kaempferol3-O-[2-O"-(E)-p-coumaroyl][beta-D-glucopyranosyl-(1-3)-O-alpha-L-rhamnopyranosyl-(1→6)-O-beta-D-glucopyranoside]('new material 33') was treated at a concentration of 100 μg/ml each, and was reacted for 48 hours. After completion of the reaction, the culture medium was collected and subjected to ELISA analysis. At this time, α-bisabolol, which is a material frequently used as an anti-inflammation agent and an abirritant, was used as a control. $PGE_2$ used Assay Design's kit and IL-6 and IL-8 used Endogen's kit, and the experiment was conducted according to the method specified in each company's manual. The inhibitory effect was calculated according to Equation 1 below, and the measurement results are shown in Table 3 below. ('33' means new material 33)

Inhibitory effect={1−(test sample−control)/($H_2O_2$−control)}×100     <Equation 1>

TABLE 2

|  | $PGE_2$ (pg/ml) | IL-6 (pg/ml) | IL-8 (pg/ml) |
|---|---|---|---|
| $H_2O_2$ (500 uM) | 350 | 245 | 290 |
| Control (a-bisabolol) | 205 | 180 | 200 |
| $H_2O_2$ + 33 (100 μg/ml) | 231 | 198 | 210 |
| Inhibitory Effect according to Equation 1 of 33 | 82.07 | 72.31 | 88.89 |

As shown in Table 2 above, the new material 33 has an effect of reducing PGE2, IL-6 and IL-8, which are increased by $H_2O_2$. This means that the new material 33 has an anti-inflammatory effect, respectively, and thus it was confirmed that the new material 33 could be used for the purpose of prevention, treatment, improvement of each inflammation.

[Experimental Example 2] Skin Accumulation Stimulation Experiment

Human repeated insult patch tests (HRIPT) were performed to confirm the skin accumulation stimulation of the kaempferol3-O-[2-O"-(E)-p-coumaroyl][beta-D-glucopyranosyl-(1→3)-O-alpha-L-rhamnopyranosyl-(1→6)-O-beta-D-glucopyranoside] and to calculate the concentration range available for the skin.

Specifically, 15 healthy adult subjects were randomly selected, and the test composition (the skin composition including an emulsifier, a stabilizer, purified water, etc. in addition to the compound) containing 0.5 wt %, 1 wt %, and 3 wt % of the compound was added dropwise by 20 μl per chamber (IQ chamber, Epitest Ltd, Finland). After 24 hours from patching the upper right part of the back of a subject, it was replaced with the new patch. A total of 9 patches were conducted, three times a week for total 3 weeks, in such manner, the skin reactions before and after patch were examined every time, and the skin reactions until 48 hours after removing the final patch were observed, and the average reactivity was observed. The results are shown in Table 3 below.

TABLE 3

| Test substance and content | Number of subjects with ±, +, or ++ reactivity (Unit: person) | | | | | | | | | Average reactivity |
|---|---|---|---|---|---|---|---|---|---|---|
|  | 1st | 2nd | 3rd | 4th | 5th | 6th | 7th | 8th | 9th |  |
| Control | 0 | 0 | 0 | 0 | 0 | 0 | 0 | 0 | 0 | 0 |
|  | 0 | 0 | 0 | 0 | 0 | 0 | 0 | 0 | 0 |  |
|  | 0 | 0 | 0 | 0 | 0 | 0 | 0 | 0 | 0 |  |
| 0.5 wt % of new material 33 | 0 | 0 | 0 | 0 | 0 | 0 | 0 | 0 | 0 | 0 |
|  | 0 | 0 | 0 | 0 | 0 | 0 | 0 | 0 | 0 |  |
|  | 0 | 0 | 0 | 0 | 0 | 0 | 0 | 0 | 0 |  |
| 1 wt % of new material 33 | 0 | 0 | 0 | 0 | 0 | 0 | 0 | 0 | 0 | 0 |
|  | 0 | 0 | 0 | 0 | 0 | 0 | 0 | 0 | 0 |  |
|  | 0 | 0 | 0 | 0 | 0 | 0 | 0 | 0 | 0 |  |
| 3 wt % of new material 33 | 0 | 0 | 0 | 0 | 0 | 0 | 0 | 0 | 0 | 0 |
|  | 0 | 0 | 0 | 0 | 0 | 0 | 0 | 0 | 0 |  |
|  | 0 | 0 | 0 | 0 | 0 | 0 | 0 | 0 | 0 |  |

[[Reactivity]]
−: negative (no response)
±: doubtful or slight erythema, etc.
+: weak reaction (which is accompanied with no phlyctenule), erythema, papule
++: severe reaction (which is accompanied with phlyctenule), erythema, papule, phlyctenule
+++: strong reaction, bullae reaction

[[Average reactivity equation]]
Average Reactivity = [{(total sum of the values obtained by multiplying the number of the examinees who exhibited the reactivity and the reaction index)/(total number of the examinees X highest point (4 point))} × 100]/number of examinations (9 tests).
In the equation, if the reactivity is −, the reaction index is 0, if the reactivity is ±, the reaction index is 1, if the reactivity is +, the reaction index is 2, and if the reactivity is ++, the reaction index is 4.
When the average reactivity is less than 3, it is considered as a stable composition.

The skin response was determined according to the criteria of the International Contact Dermatitis Research Group (ICDRG). 'New material 33' in the table above is kaempferol3-O-[2-O"-(E)-p-coumaroyl][beta-D-glucopyranosyl-(1→3)-O-alpha-L-rhamnopyranosyl-(1→6)-O-beta-D-glucopyranoside]. That is, all the substance showed (−) reactivity in the content range (no subject showed ±, +, ++, or +++ reactivity), through which it was confirmed that the substances have no cumulative irritation of the skin and can be used safely on the skin.

Hereinafter, formulation examples of the composition according to an aspect of the present disclosure will be explained, but the scope of the present disclosure is not limited thereto.

[Formulation Example 1] Soft Capsule 10 mg of kaempferol3-O-[2-O"-(E)-p-coumaroyl][beta-D-glucopyranosyl-(1→3)-O-alpha-L-rhamnopyranosyl-(1→6)-O-beta-D-glucopyranoside], 80-140 mg of L-carnitine, 180 mg of soybean oil, 2 mg of palm oil, 8 mg of vegetable hardened oil, 4 mg of yellow wax and 6 mg of lecithin were mixed and filled in one capsule according to a conventional method to prepare a soft capsule.

[Formulation Example 2] Tablet 10 mg of kaempferol3-O-[2-O"-(E)-p-coumaroyl][beta-D-glucopyranosyl-(1→3)-O-alpha-L-rhamnopyranosyl-(1→6)-O-beta-D-glucopyranoside], 200 mg of galactooligosaccharide, 60 mg of lactose, and 140 mg of maltose were mixed and granulated using a fluidized bed dryer, then 6 mg of sugar ester was added, and tabletted with tablet machine to prepare a tablet.

[Formulation Example 3] Granule 5 mg of kaempferol3-O-[2-O"-(E)-p-coumaroyl][beta-D-glucopyranosyl-(1→3)-O-alpha-L-rhamnopyranosyl-(1→6)-O-beta-D-glucopyranoside], 250 mg of anhydrous crystalline glucose and 550 mg of starch were mixed, molded into granules using a fluidized bed granulator, and then filled into pouch to prepare a granule.

[Formulation Example 4] Drink 2 mg of kaempferol3-O-[2-O"-(E)-p-coumaroyl][beta-D-glucopyranosyl-(1→3)-O-alpha-L-rhamnopyranosyl-(1→6)-O-beta-D-glucopyranoside], 10 g of glucose, 0.6 g of citric acid, and 25 g of liquid oligosaccharides were mixed, and then 300 ml of purified water was added. Each bottle was filled with 200 ml. After the bottle was filled, they were sterilized at 130° C. for 4-5 seconds to prepare a drink.

[Formulation Example 5] Injection 20 mg of kaempferol3-O-[2-O"-(E)-p-coumaroyl][beta-D-glucopyranosyl-(1→3)-O-alpha-L-rhamnopyranosyl-(1→6)-O-beta-D-glucopyranoside], a suitable amount of sterile distilled water for injection, and a suitable amount of a pH adjusting agent were used to prepare an injection in a conventional method.

[Formulation Example 6] Health Food

The health food was prepared in a conventional method according to the composition shown in Table 4 below.

TABLE 4

| Components | Contents |
| --- | --- |
| Kaempferol3-O-[2-O"-(E)-p-coumaroyl][beta-D-glucopyranosyl-(1→3)-O-alpha-L-rhamnopyranosyl-(1→6)-O-beta-D-glucopyranoside] | 0.5 mg |
| Vitamin mixture | |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| calcium pantothenate | 0.5 mg |
| Mineral mixture | |
| ferrous sulfate | 1.75 mg |
| zinc oxide | 0.82 mg |
| Magnesium carbonate | 25.3 mg |
| Potassium dihydrogen phosphate | 15 mg |
| Dibasic calcium phosphate | 55 mg |
| Potassium citrate | 90 mg |
| Calcium carbonate | 100 mg |
| Magnesium chloride | 24.8 mg |

Although the composition ratio of the vitamin and inorganic mixture was obtained by a mixed composition using the components that are relatively suitable for health foods, the compounding ratio may be arbitrarily modified. The above ingredients may be mixed according to the conventional method for preparing health foods, and then may be used for preparing a health food composition according to the conventional method.

[Formulation Example 7] Health Drink

TABLE 5

| Components | Contents |
| --- | --- |
| Kaempferol3-O-[2-O"-(E)-p-coumaroyl][beta-D-glucopyranosyl-(1→3)-O-alpha-L-rhamnopyranosyl-(1→6)-O-beta-D-glucopyranoside] | 2 mg |
| Citric acid | 1000 mg |
| Oligosaccharide | 100 g |
| Plum concentrate | 2 g |
| Taurine | 1 g |
| Purified water | balance |
| Total volume | 900 ml |

As shown in Table 5 above, the balance of purified water was added to make a total volume of 900 ml, and the above components were mixed according to the conventional method for preparing a healthy beverage. The mixture was stirred and heated at 85° C. for about 1 hour, and then the resulting solution was filtered, obtained in a sterilized 2 liter container, sterilized and sealed, and then refrigerated to prepare a health drink.

[Formulation Example 8] Softening Tonic (Skin Lotion)

0.2 wt % of kaempferol3-O-[2-O"-(E)-p-coumaroyl][beta-D-glucopyranosyl-(1→3)-O-alpha-L-rhamnopyranosyl-(1→6)-O-beta-D-glucopyranoside], 1.00 wt % of L-ascorbic acid-2-magnesium phosphate salt, 5.00 wt % of water-soluble collagen (1% aqueous solution), 0.10 wt % of sodium citrate, 0.05 wt % of citric acid, 0.20 wt % of licorice extract, 3.00 wt % of 1,3-butylene glycol, and the residual quantity of purified water were used to prepare softening tonic (skin lotion).

[Formulation Example 9] Cream Formulation 0.2 wt % of kaempferol3-O-[2-O"-(E)-p-coumaroyl][beta-D-glucopyranosyl-(1→3)-O-alpha-L-rhamnopyranosyl-(1→6)-O-beta-D-glucopyranoside], 2.00 wt % of polyethyleneglycol monostearate, 5.00 wt % of self-emulsifying glycerin monostearate, 4.00 wt % of propylene glycol, 6.00 wt % of squalene, 6.00 wt % of tri2-ethylhexaneglyceryl, 1.00 wt % of sphingoglycolipid, 7.00 wt % of 1,3-butylene glycol, 5.00 wt % of beeswax, and the balance of purified water were used to prepare a cream preparation.

[Formulation Example 10] Pack

0.2 wt % of kaempferol3-O-[2-O"-(E)-p-coumaroyl][beta-D-glucopyranosyl-(1→3)-O-alpha-L-rhamnopyranosyl-(1→6)-O-beta-D-glucopyranoside], 21.00 wt % of polyvinyl alcohol, 3.00 wt % of L-ascorbic acid-2-magnesium phosphate, 5.00 wt % of lauroylhydroxyproline, 8.00 wt % of water-soluble collagen (1% aqueous solution), 7.00 wt % of 1,3-butylene glycol, 7.00 wt % of ethanol, and the balance of purified water were used to prepare a composition and then to prepare a pack.

From the foregoing, the present disclosure has been described with reference to the specific embodiments of the present specification, and it is apparent to those skilled in the art that these specific techniques are only preferred embodiments, which are not intended to limit the scope of the present specification. Accordingly, the substantial scope of the present specification will be defined by the appended claims and equivalents thereof.

The invention claimed is:

1. A method for treating inflammation comprising administering a compound of following Formula 1, an optical isomer thereof, a pharmaceutically acceptable salt thereof, a hydrate thereof, or a solvate thereof as an active ingredient to a subject in need treating inflammation:

[Formula 1]

(In Formula 1 above, $R_1$ is $C_{15}H_9O_6$, $R_2$ is $C_6H_{11}O_5$, and $R_3$ is $C_9H_7O_2$), wherein the compound of Formula 1, the optical isomer thereof, the pharmaceutically acceptable salt thereof, the hydrate thereof, or the solvate thereof is obtained by separating from a post-fermented tea-extract.

2. The method of claim 1, wherein the Ri is represented by following Formula 2:

[Formula 2]

3. The method of claim 1, wherein the R2 is represented by following Formula 3:

[Formula 3]

4. The method of claim 1, wherein the R3 is represented by following Formula 4:

[Formula 4]

5. The method of claim 1, wherein the compound is kaempferol3-O -[2-O"-(E)-p-coumaroyl] [beta-D-glucopyranosyl-(1→3)-O-alpha-L-rhamnopyranosyl-(1→6)-O-beta-D-glucopyranoside].

6. The method of claim 1, wherein the extract is obtained by extraction by one or more solvents selected from hydrothermal water, lower alcohols of C1 to C6, and mixed solvents thereof.

7. The method of claim 6, wherein the lower alcohol is ethanol.

8. The method of claim 1, wherein the extract is a fraction fractionated with ketones after extraction.

9. The method of claim 8, wherein the ketone is acetone.

10. The method of claim 1, wherein the compound of Formula 1, the optical isomer thereof, the pharmaceutically acceptable salt thereof, the hydrate thereof, or the solvate thereof is administered in form of a composition, and wherein the content of the compound of Formula 1, the optical isomer thereof, the pharmaceutically acceptable salt thereof, the hydrate thereof, or the solvate thereof in the composition is 0.00001% to 10% by weight based on the total weight of the composition.

11. The method of claim 1, wherein the post-fermented tea extract is administered in form of a composition, and wherein the content of the post-fermented tea extract in the composition is 0.1% to 90% by weight based on the total weight of the composition.

12. The method of claim 1, wherein the extract comprises the compound of Formula 1, the optical isomer thereof, the pharmaceutically acceptable salt thereof, the hydrate thereof, or the solvate thereof in an amount of 0.00001% to 20% by weight based on the total weight of the extract.

13. The method of claim 1, wherein a dosage of the compound of Formula 1, the isomer thereof, the pharmaceutically acceptable salt thereof, the hydrate thereof, or the solvate thereof is 0.00001 mg/kg/day to 100 mg/kg/day.

14. The method of claim 1, wherein the treating inflammation is by inhibitions of the production of one or more selected from the group consisting of PGE2 (Prostaglandin E2), IL-6 (Interleukin 6) and IL-8 (Interleukin 8).

15. The method of claim 1, wherein compound of Formula 1, the optical isomer thereof, the pharmaceutically acceptable salt thereof, the hydrate thereof, the solvate thereof, or a post-fermented tea extract comprising the same is administered in form of a composition, and wherein the composition is a food composition, a cosmetic composition, or a pharmaceutical composition.

* * * * *